US011840522B2

United States Patent
Miyauchi et al.

(10) Patent No.: US 11,840,522 B2
(45) Date of Patent: Dec. 12, 2023

(54) METHOD OF STABILIZING PERFLUORO(2-METHYLENE-4-METHYL-1,3-DIOXOLANE) AND COMPOSITION CONTAINING STABILIZED PERFLUORO(2-METHYLENE-4-METHYL-1,3-DIOXOLANE)

(71) Applicants: TOSOH CORPORATION, Shunan (JP); TOSOH FINECHEM CORPORATION, Shunan (JP)

(72) Inventors: Hideki Miyauchi, Shunan (JP); Shota Nishida, Shunan (JP); Daisuke Inoue, Shunan (JP); Yusuke Shigeta, Shunan (JP); Norihisa Kondo, Shunan (JP); Makoto Watanabe, Yokkaichi (JP); Shohei Yumino, Yokkaichi (JP); Tomoya Shimono, Yokkaichi (JP)

(73) Assignees: TOSOH CORPORATION, Shunan (JP); TOSOH FINECHEM CORPORATION, Shunan (JP)

( * ) Notice: Subject to any disclaimer, the term of this patent is extended or adjusted under 35 U.S.C. 154(b) by 0 days.

(21) Appl. No.: 17/416,206

(22) PCT Filed: Dec. 20, 2019

(86) PCT No.: PCT/JP2019/050014
§ 371 (c)(1),
(2) Date: Jun. 18, 2021

(87) PCT Pub. No.: WO2020/130122
PCT Pub. Date: Jun. 25, 2020

(65) Prior Publication Data
US 2022/0056006 A1 Feb. 24, 2022

(30) Foreign Application Priority Data
Dec. 20, 2018 (JP) .................... 2018-238590

(51) Int. Cl.
*C07D 317/42* (2006.01)
*C07B 63/04* (2006.01)

(52) U.S. Cl.
CPC .......... *C07D 317/42* (2013.01); *C07B 63/04* (2013.01)

(58) Field of Classification Search
CPC ................................................. C07D 317/42
See application file for complete search history.

(56) References Cited

U.S. PATENT DOCUMENTS 2,737,533 A 3/1956 Mark et al.
6,639,039 B1 10/2003 Fries et al.
(Continued)

FOREIGN PATENT DOCUMENTS

DE 10 2007 029 869 A1 1/2008
DE 102007029869 A1 * 1/2008 ............. C07B 63/04
(Continued)

OTHER PUBLICATIONS

Zhu "Scales of Oxidation Potentials, pKa, and BDE of Various Hydroquinones and Catechols in DMSO" J. Org. Chem. 2010, 75, 7240-7257.*

(Continued)

*Primary Examiner* — David K O'Dell
(74) *Attorney, Agent, or Firm* — Oblon, McClelland, Maier & Neustadt, L.L.P.

(57) ABSTRACT

A method of stabilizing perfluoro(2-methylene-4-methyl-1,3-dioxolane) (hereinafter simply referred to as a "stabilization method"), including incorporating at least one selected from the group consisting of a hydroxy group-containing fluoroaromatic compound represented by General Formula (1) below and a hydroxy group-containing fluoroaromatic compound represented by General Formula (2) below into a composition containing perfluoro(2-methylene-4-methyl-1,3-dioxolane):

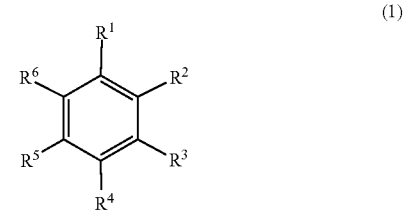

(1)

(in the formula, $R^1$ to $R^6$ each independently represent one selected from the group consisting of a fluorine atom, a perfluoroalkyl group and a hydroxy group, and at least one of $R^1$ to $R^6$ is a hydroxy group);

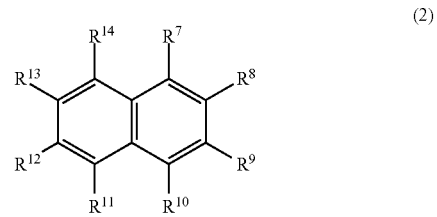

(2)

(in the formula, $R^7$ to $R^{14}$ each independently represent one selected from the group consisting of a fluorine atom, a perfluoroalkyl group and a hydroxy group, and at least one of $R^7$ to $R^{14}$ is a hydroxy group).

20 Claims, No Drawings

(56) References Cited

U.S. PATENT DOCUMENTS

| | | | |
|---|---|---|---|
| 11,274,168 B2 * | 3/2022 | Saito .................. | H01M 8/1032 |
| 2019/0185600 A1 | 6/2019 | Saito et al. | |
| 2021/0214332 A1 | 7/2021 | Miyauchi et al. | |

FOREIGN PATENT DOCUMENTS

| | | | |
|---|---|---|---|
| JP | 50-7046 A | 3/1975 | |
| JP | WO 2018/062193 A1 | 4/2018 | |

OTHER PUBLICATIONS

International Search Report and Written Opinion dated Mar. 10, 2020 in PCT/JP2019/050014, 8 pages.
International Preliminary Report on Patentability dated Jul. 1, 2021 in PCT/JP2019/050014 (with English translation), 11 pages.
Okamoto, Y. et al., "New amorphous perfluoro polymers: perfluoroxolane polymers for use as plastic optical fibers and gas separation membranes", Polym. Adv. Technol. 2016, 27 , pp. 33-41.
Extended European Search Report dated Jul. 22, 2022 in European Patent Application No. 19899648.0, 6 pages.

* cited by examiner

METHOD OF STABILIZING PERFLUORO(2-METHYLENE-4-METHYL-1,3-DIOXOLANE) AND COMPOSITION CONTAINING STABILIZED PERFLUORO(2-METHYLENE-4-METHYL-1,3-DIOXOLANE)

This application is a National Stage (371) of PCT/JP2019/050014, filed Dec. 20, 2019, which claims priority to JP 2018-238590, filed Dec. 20, 2018.

TECHNICAL FIELD

The present invention relates to a method of stabilizing perfluoro(2-methylene-4-methyl-1,3-dioxolane) and a composition containing stabilized perfluoro(2-methylene-4-methyl-1,3-dioxolane).

BACKGROUND ART

Perfluoro(2-methylene-4-methyl-1,3-dioxolane) can be radically polymerized in the presence of an initiator and is used as a synthetic raw material for poly[(perfluoro(2-methylene-4-methyl-1,3-dioxolane)]. Poly[(perfluoro(2-methylene-4-methyl-1,3-dioxolane)] is prospective as a resin for a gas separation membrane and a transparent resin for optical fibers. Specifically, poly[(perfluoro(2-methylene-4-methyl-1,3-dioxolane)] is a transparent polymer having an amorphous structure and has a high glass transition temperature (133° C. to 136° C.), and thus is expected to be a next-generation resin for optical fibers and a resin for a gas separation membrane (NPL 1).

Meanwhile, for the purpose of stabilizing fluorine-containing monomers during storage, addition of a general polymerization inhibitor, such as a terpene compound described in PTL 1 and a phenolic compound described in PTL 2, has been conventionally studied. In addition, PTL 3 discloses a 6-membered ring unsaturated hydrocarbon having a t-butyl group or the like as a polymerization inhibitor for ring structure monomers including perfluoro(2-methylene-4-methyl-1,3-dioxolane).

[PTL 1] U.S. Pat. No. 2,737,533
[PTL 2] Japanese Examined Patent Publication No. S50-7046
[PTL 3] WO 2018/062193
[NPL 1] Y. Okamoto, et. al., Polym. Adv. Technol. 2016, 27 33-41

SUMMARY OF INVENTION

In the above applications in which application of poly [(perfluoro(2-methylene-4-methyl-1,3-dioxolane)] is expected, it is necessary to control the molecular weight and polymer properties according to applications. Therefore, it is desirable to use perfluoro(2-methylene-4-methyl-1,3-dioxolane) as raw material monomers in a polymerization reaction while inhibiting a polymerization reaction, a decomposition reaction, and the like during storage and maintaining the quality of the monomers. In the case of perfluoro(2-methylene-4-methyl-1,3-dioxolane), in addition to inhibition of a polymerization reaction during storage, high quality stability such as anti-coloring is required particularly in optical applications such as optical fibers. Therefore, a superior method for stabilizing perfluoro(2-methylene-4-methyl-1,3-dioxolane) and a composition containing stabilized perfluoro(2-methylene-4-methyl-1,3-dioxolane) are desired.

In view of the above circumstances, one aspect of the present invention provides a composition containing stabilized perfluoro(2-methylene-4-methyl-1,3-dioxolane) and specifically, provides a composition containing perfluoro(2-methylene-4-methyl-1,3-dioxolane) which is unlikely to cause quality changes such as a polymerization reaction and coloring during storage.

The present inventors conducted extensive studies regarding a method of stabilizing a composition containing perfluoro(2-methylene-4-methyl-1,3-dioxolane) and as a result, found that, when a composition containing perfluoro(2-methylene-4-methyl-1,3-dioxolane) contains a hydroxy group-containing fluoroaromatic compound having a specific structure, it is possible to suppress quality changes such as a polymerization reaction and coloring during storage, and completed the present invention. That is, the present invention relates to the following aspects.

[1] A method of stabilizing perfluoro(2-methylene-4-methyl-1,3-dioxolane) (hereinafter simply referred to as a "stabilization method"), including incorporating at least one selected from the group consisting of a hydroxy group-containing fluoroaromatic compound represented by General Formula (1) below and a hydroxy group-containing fluoroaromatic compound represented by General Formula (2) below into a composition containing perfluoro(2-methylene-4-methyl-1,3-dioxolane):

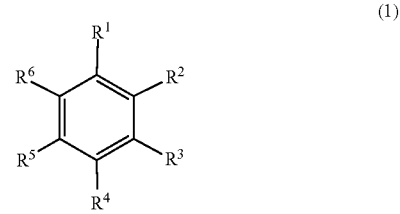

(1)

(in the formula, $R^1$ to $R^6$ each independently represent one selected from the group consisting of a fluorine atom, a perfluoroalkyl group and a hydroxy group, and at least one of $R^1$ to $R^6$ is a hydroxy group);

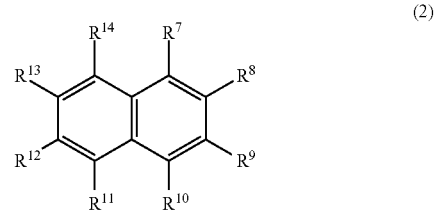

(2)

(in the formula, $R^7$ to $R^{14}$ each independently represent one selected from the group consisting of a fluorine atom, a perfluoroalkyl group and a hydroxy group, and at least one of $R^7$ to $R^{14}$ is a hydroxy group).

[2] The method of stabilizing perfluoro(2-methylene-4-methyl-1,3-dioxolane) according to [1], wherein the hydroxy group-containing fluoroaromatic compound contains perfluoro hydroquinone.

[3] The method of stabilizing perfluoro(2-methylene-4-methyl-1,3-dioxolane) according to [1] or [2], including maintaining the temperature at 0° C. or lower.

[4] A composition containing perfluoro(2-methylene-4-methyl-1,3-dioxolane) including at least one selected from the group consisting of a hydroxy group-containing fluoroaromatic compound represented by General Formula (1)

above and a hydroxy group-containing fluoroaromatic compound represented by General Formula (2) above.

[5] The composition containing perfluoro(2-methylene-4-methyl-1,3-dioxolane) according to [4], which contains 0.1 to 2,000 ppm of the hydroxy group-containing fluoroaromatic compound in terms of weight ratio.

[6] The composition containing perfluoro(2-methylene-4-methyl-1,3-dioxolane) according to [4] or [5], wherein the hydroxy group-containing fluoroaromatic compound contains perfluoro hydroquinone.

According to one aspect of the present invention, it is possible to provide a composition containing perfluoro(2-methylene-4-methyl-1,3-dioxolane) which is unlikely to cause quality changes such as a polymerization reaction and coloring during storage.

DESCRIPTION OF EMBODIMENTS

In a stabilization method of the present invention, into a composition containing perfluoro(2-methylene-4-methyl-1,3-dioxolane), at least one selected from the group consisting of a hydroxy group-containing fluoroaromatic compound represented by General Formula (1) and a hydroxy group-containing fluoroaromatic compound represented by General Formula (2) is incorporated. Therefore, the progress of a polymerization reaction of perfluoro(2-methylene-4-methyl-1,3-dioxolane) during storage can be suppressed and coloring can also be suppressed.

Only one of the hydroxy group-containing fluoroaromatic compound represented by General Formula (1) and the hydroxy group-containing fluoroaromatic compound represented by General Formula (2) can be used, or two or more thereof can be used in combination at any ratio. Such a hydroxy group-containing fluoroaromatic compound can function as a stabilizer that can contribute to stabilization of perfluoro(2-methylene-4-methyl-1,3-dioxolane).

In General Formula (1), $R^1$ to $R^6$ each independently represent one selected from the group consisting of a fluorine atom, a perfluoroalkyl group and a hydroxy group, and at least one of $R^1$ to $R^6$ is a hydroxy group. In General Formula (2), $R^7$ to $R^{14}$ each independently represent one selected from the group consisting of a fluorine atom, a perfluoroalkyl group and a hydroxy group, and at least one of $R^7$ to $R^{14}$ is a hydroxy group. That is, the hydroxy group-containing fluoroaromatic compound used in the stabilization method of the present invention have one or more hydroxy groups in the molecule or may have two or more hydroxy groups in the molecule. The number of hydroxy groups contained in the molecule can be, for example, 1 to 3, and is preferably 2. When the hydroxy group-containing fluoroaromatic compound has two hydroxy groups, a sufficient stabilization effect is exhibited and the hydroxy group-containing fluoroaromatic compound tends not to dissolve well in perfluoro(2-methylene-4-methyl-1,3-dioxolane), and thus it can be subjected to a polymerization reaction by performing only a simple operation such as filtration as necessary.

In addition, since the compound represented by General Formula (1) is a fluorine-containing compound, $R^1$ to $R^6$ are not all hydroxy groups, and at least one of $R^1$ to $R^6$ represents a fluorine atom or a perfluoroalkyl group. Since the compound represented by General Formula (2) is also a fluorine-containing compound, $R^7$ to $R^{14}$ are not all hydroxy groups and at least one of $R^7$ to $R^{14}$ represents a fluorine atom or a perfluoroalkyl group. The hydroxy group-containing fluoroaromatic compound used in the stabilization method of the present invention can have one or more fluorine atoms in the molecule, and can also have two or more fluorine atoms in the molecule. In addition, the hydroxy group-containing fluoroaromatic compound used in the stabilization method of the present invention can have one or more perfluoroalkyl groups in the molecule and can also have two or more perfluoroalkyl groups in the molecule. The perfluoroalkyl group is a monovalent group that can be represented by $C_nF_{2n+1}$, where n can be an integer range of 1 to 6.

Specific examples of hydroxy group-containing fluoroaromatic compounds used in the stabilization method of the present invention include the following example compounds, but the present invention is not limited thereto.

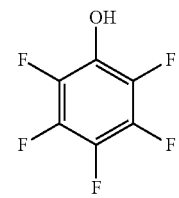

1-1

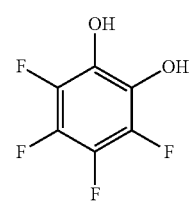

1-2

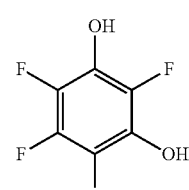

1-3

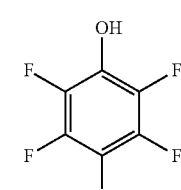

1-4

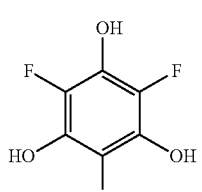

1-5

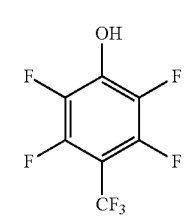

1-6

1-7 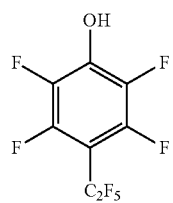

1-8 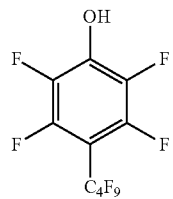

1-9 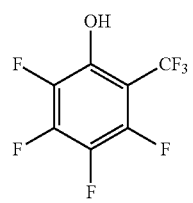

1-10 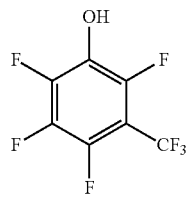

2-1 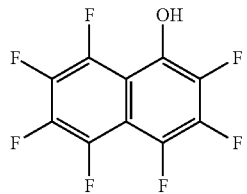

2-2 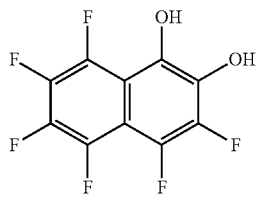

2-3 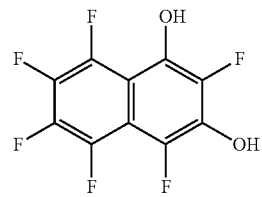

2-4 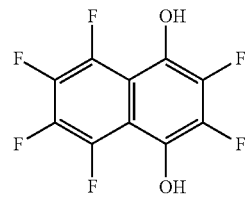

2-5 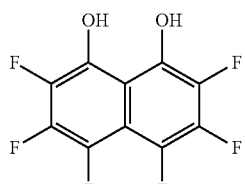

2-6 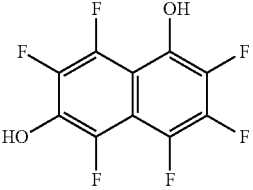

2-7 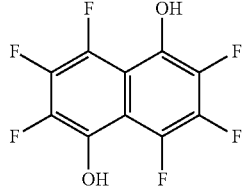

2-8 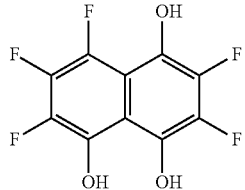

The amount of the hydroxy group-containing fluoroaromatic compound added is preferably 0.1 to 2,000 ppm and more preferably 1 to 1,000 ppm (weight ratio) with respect to perfluoro(2-methylene-4-methyl-1,3-dioxolane). When the amount added is set to 0.1 ppm or more, a better stabilization effect can be obtained. On the other hand, even if the amount added exceeds 2,000 ppm, further improvement in the stabilization effect tends not to be obtained, and an operation of removing the hydroxy group-containing fluoroaromatic compound when a polymerization reaction is performed may be complicated. The added hydroxy group-containing fluoroaromatic compound may be dissolved in the composition containing perfluoro(2-methylene-4-methyl-1,3-dioxolane), or the compound can exhibit a stabilization effect without any problem even if it precipitates or phase-separates without dissolving.

Perfluoro(2-methylene-4-methyl-1,3-dioxolane), which is a target to be stabilized by the stabilization method of the present invention, can be represented by the following formula (A).

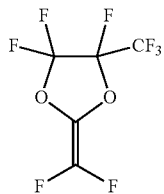

(A)

Perfluoro(2-methylene-4-methyl-1,3-dioxolane) can be obtained by, for example, a method in which perfluoro(2,4-dimethyl-2-fluoroformyl-1,3-dioxolane) obtained by reacting trifluoromethylpyruvic acid fluoride monomers or its dimers with hexafluoropropylene oxide in the presence of cesium fluoride is hydrolyzed and neutralized and the obtained alkali metal salts are then decarboxylated. Such a method is known in the literature, and is described in, for example, Macromolecules 2005, 38, 4237-4245.

In addition, in the present invention, "composition containing perfluoro(2-methylene-4-methyl-1,3-dioxolane)" is a composition containing at least a pure product of perfluoro(2-methylene-4-methyl-1,3-dioxolane), or may be a mixture containing by-products and the like produced in the process of synthesizing perfluoro(2-methylene-4-methyl-1,3-dioxolane) in addition to the pure product. By adding one or more of the hydroxy group-containing fluoroaromatic compounds to such a composition, it is possible to stabilize perfluoro(2-methylene-4-methyl-1,3-dioxolane). In this context, examples of by-products produced in the synthesis process include 2-hydro-perfluoro(2,4-dimethyl-1,3-dioxolane) (the following Formula (B)).

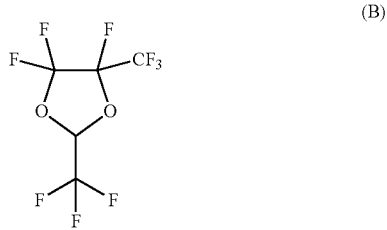 [SMILES: FC(F)(F)C1OC(F)(F)C(F)(C(F)(F)F)O1]

(B)

Generally, the content of such by-products is less than 10% (weight ratio) with respect to perfluoro(2-methylene-4-methyl-1,3-dioxolane). In addition, in the present invention, in the composition containing perfluoro(2-methylene-4-methyl-1,3-dioxolane), perfluoro(2-methylene-4-methyl-1,3-dioxolane) may be diluted with a solvent. The solvent in this case is not particularly limited, and a solvent in which perfluoro(2-methylene-4-methyl-1,3-dioxolane) dissolves, and which does not react with perfluoro(2-methylene-4-methyl-1,3-dioxolane), and does not inhibit a polymerization reaction in the next process is preferable. Specific examples of preferable solvents include fluorine-containing solvents which contain fluorinated chain alkanes such as perfluorohexane, $C_6F_{13}C_2H_5$, and $C_2F_5CHFCHFCF_3$, fluorinated cyclic alkanes such as $c-C_5F_7H_3$, fluorinated aromatic compounds such as hexafluorobenzene, trifluoromethylbenzene, and perfluorotoluene, fluoroalkyl ethers such as $CF_3CH_2OCF_2CF_2H$, $C_4F_9OCH_3$, $C_4F_9OC_2H_5$, and $C_6F_{13}OCH_3$, and fluorinated alkylamines such as perfluorotripropylamine and perfluorotributylamine. The amount of the solvent used is preferably a weight ratio of 0.1 to 10 times with respect to the amount of perfluoro(2-methylene-4-methyl-1,3-dioxolane).

In the present invention, examples of container materials used when the composition containing perfluoro(2-methylene-4-methyl-1,3-dioxolane) is stored and transported include a resin container made of polyethylene, polypropylene, or polytetrafluoroethylene, a metal container made of stainless steel, a glass container, and a composite container made of a resin and a metal, and a resin container and a composite container made of a resin and a metal are preferable in consideration of corrosion resistance and the like.

In addition, it is preferable that a container is filled with perfluoro(2-methylene-4-methyl-1,3-dioxolane) and then a gas phase part in the container is filled with an inert gas such as nitrogen, argon, carbon dioxide and the like in consideration of stability and the like. In addition, when the temperature during storage and transportation is set to a low temperature condition of 0° C. or lower, the stabilization effect can be further improved. When the atmosphere temperature during storage and transportation is set to 0° C. or lower, the temperature of the composition containing perfluoro(2-methylene-4-methyl-1,3-dioxolane) can be maintained at 0° C. or lower. The atmosphere temperature during storage and transportation and the temperature of the composition containing perfluoro(2-methylene-4-methyl-1,3-dioxolane) are preferably −30° C. or higher and 10° C. or lower.

EXAMPLES

Hereinafter, the present invention will be described below in detail with reference to examples, but the present invention is not limited to these examples.

The following instrument was used for the analysis.
$^{19}$F-NMR: AVANCE II 400 (commercially available from BRUKER)
GC: GC-2025 (commercially available from Shimadzu Corporation)

Reference Example 1. Preparation of perfluoro(2,4-dimethyl-2-fluoroformyl-1,3-dioxolane)

Trifluoropyruvic acid fluoride dimers represented by the following formula (2,222.4 g, a pure content of 1,980.3 g, 6.88 mol), cesium fluoride (315.6 g, 2.08 mol) and diethylene glycol dimethyl ether (1,338.8 g, 9.98 mol) were put into a 10 L SUS316 autoclave having a stirrer with a pressure resistance of 8 MPa and cooled on an ice bath at 0° C. Next, hexafluoropropylene oxide (2,284.4 g, 13.76 mol) was added thereto over 2 hours and then heated at 120° C., and the reaction was caused for 24 hours.

Trifluoropyruvic Acid Fluoride Dimer

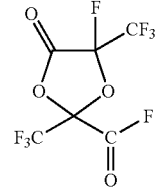

After the reaction was completed, cooling was performed to room temperature, a lower layer was separated off, and crude perfluoro(2,4-dimethyl-2-fluoroformyl-1,3-dioxolane) was obtained (yellow liquid, 3,047.4 g). In quantification by $^{19}$F-NMR using benzotrifluoride as an internal standard substance, 2,901.0 g (9.36 mol) of the following perfluoro(2,4-dimethyl-2-fluoroformyl-1,3-dioxolane), which was a target product, was produced (a yield of 68%/trifluoromethylpyruvic acid fluoride dimer standard). The obtained target product was a mixture of two kinds of diastereomers at a ratio of 6/4 (molar ratio).

$^{19}$F-NMR (neat, 376 MHz) (isomer 1) δ23.63, −77.76 (d, J=131.6 Hz), −80.13, −81.57, −83.56 (d, J=135.4 Hz), −124.91. (isomer 2) δ23.16, −78.45 (d, J=131.6 Hz), −80.37, −81.56, −84.05 (d, J=139.1 Hz), −123.72.

Perfluoro(2,4-dimethyl-2-fluoroformyl-1,3-dioxolane)

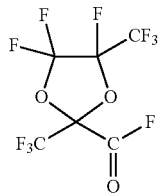 [SMILES: O=C(F)C1(C(F)(F)F)OC(F)(F)C(F)(C(F)(F)F)O1]

Reference Example 2. Preparation of perfluoro(2,4-dimethyl-1,3-dioxolane-2-yl)carboxylic Acid Potassium Salt Aqueous Solution Potassium carbonate (659.8 g, 4.77 mol) and water (1,400 mL) were put into a 10 L glass three-neck round-bottom flask having a stirrer and a dropping funnel and dissolved with stirring and then cooled on an ice bath at 0° C. Next, perfluoro(2,4-dimethyl-2-fluoroformyl-1,3-dioxolane) (1,510.2 g, a pure content of 1,450.5 g, 4.68 mol) prepared in Reference Example 1 was added dropwise thereto over 2 hours while controlling heat generation in a temperature range of 0° C. to 10° C., and the mixture was then additionally stirred at the same temperature for 1 hour and left for 1 hour, a lower layer was then separated, and 2,703 g of an aqueous solution containing a target product perfluoro (2,4-dimethyl-1,3-dioxolane-2-yl)carboxylic acid potassium salt was obtained (a pure content of 1,602.2 g, 4.63 mol, a yield of 99% according to quantitative analysis by $^{19}$F-NMR using benzotrifluoride as an internal standard substance).

perfluoro(2,4-dimethyl-1,3-dioxolane-2-yl)carboxylic Acid Potassium Salt

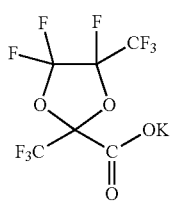

Reference Example 3. Synthesis of perfluoro(2-methylene-4-methyl-1,3-dioxolane)

The perfluoro(2,4-dimethyl-1,3-dioxolane-2-yl)carboxylic acid potassium salt aqueous solution (270 g, pure content 160.2 g, 0.463 mol) obtained in Reference Example 2, diethylene glycol dimethyl ether (320 g) and a 30 weight % potassium carbonate aqueous solution (120 g) were put into a 1 L three-neck round-bottom flask, the mixture was stirred for 0.5 hours and left for 0.5 hours, and an upper layer was then separated from the reaction product separated into two layers by a liquid separation operation. Next, the separated upper layer was put into a 1 L glass three-neck round-bottom flask having a stirrer and a distillation device and heated on an oil bath at 60° C., and the contained water was azeotropically evaporated with diethylene glycol dimethyl ether at a pressure of 13 kPa to 1 kPa while gradually increasing the degree of decompression, and 411.5 g of the diethylene glycol dimethyl ether solution containing a perfluoro(2,4-dimethyl-1,3-dioxolane-2-yl)carboxylic acid potassium salt was obtained (a target product content of 158.8 g, 0.459 mol, a water content of 0.06 weight %). Next, liquid paraffin (commercially available from FUJIFILM Wako Pure Chemical Corporation, an initial boiling point 300° C., 159 g) was put into a 1 L glass three-neck round-bottom flask having a stirrer, a dropping funnel and a distillation device with a cold trap (two stages at −20° C. and −78° C.), and under a reduced pressure of 30 kPa, heating was performed at 130° C. with stirring, and the diethylene glycol dimethyl ether solution (411.5 g) containing the perfluoro(2,4-dimethyl-1,3-dioxolane-2-yl)carboxylic acid potassium salt was then added dropwise thereto over 3 hours, and the mixture was additionally left under the same reduced pressure and at the same temperature for 1 hour. After the reaction was completed, the product collected in the cold trap (99.66 g) was analyzed by $^{19}$F-NMR using benzotrifluoride as an internal standard substance, and thus it was confirmed that 92.96 g (0.381 mol, a yield of 83%) of perfluoro(2-methylene-4-methyl-1,3-dioxolane) was produced. The amount of 2-hydro-perfluoro(2,4-dimethyl-1,3-dioxolane) produced was 3.64 g (a yield of 3.0%).

The product collected in the cold trap was put into a 200 mL round-bottom flask having a distillation device composed of rectifying columns of 10 steps Kiriyama Pac and a stirring bar, and precision distillation was performed under atmospheric pressure at a distribution ratio of 10/1 to obtain purified perfluoro(2-methylene-4-methyl-1,3-dioxolane) (a boiling point of 43° C. to 44° C., 76.2 g, a purity of 98.2%). $^{19}$F-NMR (CDCl$_3$, 376 MHz) δ−82.08 (m), −83.90 (dq, J=136.3 Hz, 7.5 Hz), −90.30 (dq, J=136.3 Hz, 5.0 Hz), −126.78 (d, J=124.1 Hz), −128.13 (dquin, J=124.1 Hz, 1.0 Hz), −130.48 (m).

Example 1

2.0 g (GC area percentage=98.2%, 2-hydro-perfluoro(2,4-dimethyl-1,3-dioxolane) GC area percentage=a content of 1.6%, and a quantitative value of perfluoro(2-methylene-4-methyl-1,3-dioxolane) according to an internal standard using hexafluorobenzene=98.3%) of perfluoro(2-methylene-4-methyl-1,3-dioxolane) obtained in Reference Example 3 was put into a 10 ml polyethylene sample bottle, and 0.0012 g (600 ppm) of perfluoro hydroquinone (Example Compound 1-4) was then added thereto, and the sample bottle was shaken. Most of the added perfluoro hydroquinone did not dissolve, and a solid remained on the bottom of the sample bottle. The sample bottle was filled with nitrogen and then sealed, and stored in a freezer set at −18° C. After 35 days, when the content was analyzed again according to an internal standard using hexafluorobenzene, the quantitative value was 98.1%, and no decrease in the content was observed. In addition, the liquid after storage was colorless and no coloring was observed.

Comparative Example 1

A test was performed in the same method as in Example 1 except that no perfluoro hydroquinone was added. After 35 days, when the content was analyzed again according to an internal standard using hexafluorobenzene, the quantitative value was 84.3%, and a decrease in the content was observed, and it was speculated that partial polymerization proceeded during storage.

Comparative Example 2

A test was performed in the same method as in Example 1 except that 2,6-di-t-butyl-p-cresol 0.0012 g (600 ppm) was added in place of perfluoro hydroquinone. After 35 days, when the content was analyzed again according to an internal standard using hexafluorobenzene, the quantitative value was 98.0%, and no decrease in the content was observed, but a liquid after storage was observed to have turned light yellow.

Comparative Example 3

A test was performed in the same method as in Example 1 except that D-limonene 0.0012 g (600 ppm) was added in place of perfluoro hydroquinone. After 35 days, when the content was analyzed again according to an internal standard using hexafluorobenzene, the quantitative value was 98.1%, and no decrease in the content was observed, but a liquid after storage was observed to have turned light yellow.

Examples 2 to 9

Tests were performed in the same method as in Example 1 except that amounts (shown in Table 1) of compounds shown in Table 1 as stabilizers were added to perfluoro(2-methylene-4-methyl-1,3-dioxolane), and a storage test was performed under conditions shown in Table 1. The results are shown in Table 1.

According to one aspect of the present invention, it is possible to perform a method of stabilizing a composition containing perfluoro(2-methylene-4-methyl-1,3-dioxolane) which is unlikely to cause quality changes such as a polymerization reaction and coloring during storage, and it is possible to obtain a composition containing stabilized perfluoro(2-methylene-4-methyl-1,3-dioxolane). The obtained composition containing perfluoro(2-methylene-4-methyl-1,3-dioxolane) can be used as a synthetic raw material for poly[(perfluoro(2-methylene-4-methyl-1,3-dioxolane)],
which is prospective as a resin for a gas separation membrane and a transparent resin for optical fibers.

This application claims priority to Japanese Patent Application No. 2018-238590 filed on Dec. 20, 2018, which is hereby expressly incorporated by reference in its entirety.

The invention claimed is:

1. A method of stabilizing perfluoro(2-methylene-4-methyl-1,3-dioxolane), comprising:
incorporating, into a composition containing perfluoro(2-methylene-4-methyl-1,3-dioxolane), at least one fluorine-containing compound selected from the group consisting of Compound 1-2, 1-3, 1-4, 1-5, 1-6, 1-7, 1-8, 1-9 and 1-10,

TABLE 1

| | PMMD (g) | Stabilizer | Amount added (g) | Storage temperature (° C.) | Quantitative value after 35 days (%) | Appearance |
|---|---|---|---|---|---|---|
| Example 1 | 2.0 | Example Compound 1-4 | 0.0012 (600 ppm) | −18 | 98.1 | Colorless |
| Comparative Example 1 | 2.0 | None | — | −18 | 84.3 | Colorless |
| Comparative Example 2 | 2.0 | BHT | 0.0012 (600 ppm) | −18 | 98.0 | Light yellow |
| Comparative Example 3 | 2.0 | D-limonene | 0.0012 (600 ppm) | −18 | 98.1 | Light yellow |
| Example 2 | 2.0 | Example Compound 1-1 | 0.0012 (600 ppm) | −18 | 97.9 | Colorless |
| Example 3 | 2.0 | Example Compound 2-1 | 0.0012 (600 ppm) | −18 | 97.7 | Colorless |
| Example 4 | 2.0 | Example Compound 1-4 | 0.0001 (50 ppm) | −18 | 98.2 | Colorless |
| Example 5 | 20.0 | Example Compound 1-4 | 0.0001 (5 ppm) | −18 | 97.8 | Colorless |
| Example 6 | 2.0 | Example Compound 1-4 | 0.0012 (600 ppm) | 0 | 97.3 | Colorless |
| Example 7 | 2.0 | Example Compound 1-4 | 0.0012 (600 ppm) | 15 | 94.7 | Colorless |
| Example 8* | 2.0 | Example Compound 1-4 | 0.0012 (600 ppm) | 0 | 97.6 | Colorless |
| Example 9 | 2.0 | Example Compound 1-6 | 0.0012 (600 ppm) | −18 | 98.0 | Colorless |

*The test was performed with dilution with 6.0 g of c-$C_5F_7H_3$ as a solvent.
PMMD: perfluoro(2-methylene-4-methyl-1,3-dioxolane)
BHT: 2,6-di-t-butyl-p-cresol

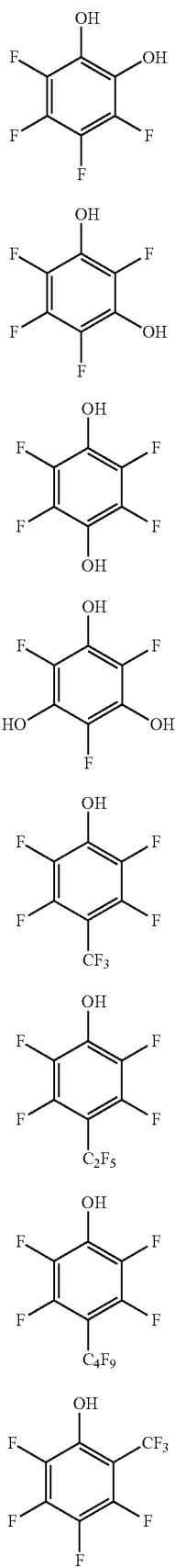

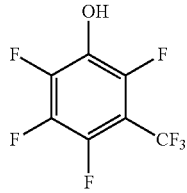

2. The method of stabilizing perfluoro(2-methylene-4-methyl-1,3-dioxolane) according to claim 1, wherein the at least one fluorine-containing compound includes perfluoro hydroquinone.

3. The method of stabilizing perfluoro(2-methylene-4-methyl-1,3-dioxolane) according to claim 1, further comprising:

maintaining a temperature at 0° C. or lower.

4. A composition containing perfluoro(2-methylene-4-methyl-1,3-dioxolane), comprising:

perfluoro(2-methylene-4-methyl-1,3-dioxolane); and at least one fluorine-containing compound selected from the group consisting of Compound 1-2, 1-3, 1-4, 1-5, 1-6, 1-7, 1-8, 1-9 and 1-10,

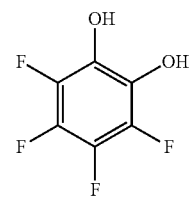

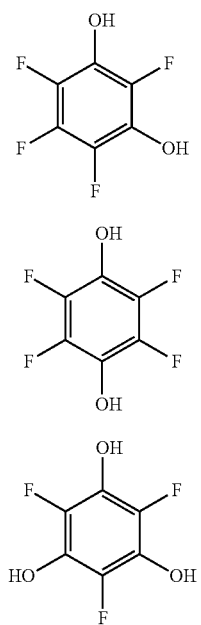

-continued

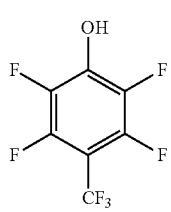
1-6

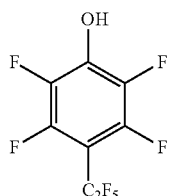
1-7

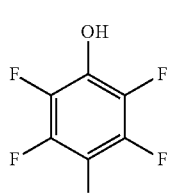
1-8

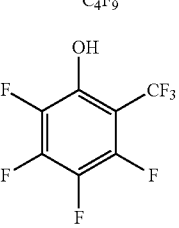
1-9

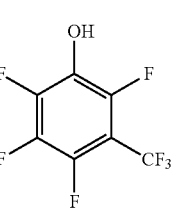
1-10

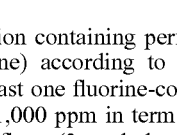

5. The composition containing perfluoro(2-methylene-4-methyl-1,3-dioxolane) according to claim 4, wherein an amount of the at least one fluorine-containing compound is in a range of 1 to 1,000 ppm in terms of weight ratio with respect to the perfluoro(2-methylene-4-methyl-1,3-dioxolane).

6. The composition containing perfluoro(2-methylene-4-methyl-1,3-dioxolane) according to claim 4, wherein the at least one fluorine-containing compound includes perfluoro hydroquinone.

7. The composition containing perfluoro(2-methylene-4-methyl-1,3-dioxolane) according to claim 5, wherein the at least one fluorine-containing compound includes perfluoro hydroquinone.

8. The method of stabilizing perfluoro(2-methylene-4-methyl-1,3-dioxolane) according to claim 2, further comprising:
maintaining a temperature at 0° C. or lower.

9. The composition containing perfluoro(2-methylene-4-methyl-1,3-dioxolane) according to claim 4, wherein an amount of the at least one fluorine-containing compound is in a range of 5 to 600 ppm in terms of weight ratio with respect to the perfluoro(2-methylene-4-methyl-1,3-dioxolane).

10. The composition containing perfluoro(2-methylene-4-methyl-1,3-dioxolane) according to claim 6, wherein an amount of the at least one fluorine-containing compound is in a range of 5 to 600 ppm in terms of weight ratio with respect to the perfluoro(2-methylene-4-methyl-1,3-dioxolane).

11. The composition containing perfluoro(2-methylene-4-methyl-1,3-dioxolane) according to claim 4, wherein the at least one fluorine-containing compound includes Compound 1-6,

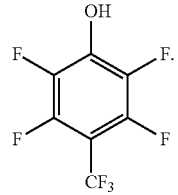
1-6

12. The composition containing perfluoro(2-methylene-4-methyl-1,3-dioxolane) according to claim 4, wherein the at least one fluorine-containing compound is at least one compound selected from the group consisting of Compound 1-6,

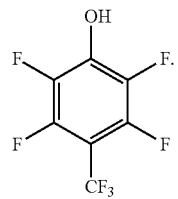
1-6

13. The composition containing perfluoro(2-methylene-4-methyl-1,3-dioxolane) according to claim 5, wherein the at least one fluorine-containing compound includes at least one compound selected from the group consisting of Compound 1-6,

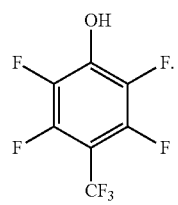
1-6

14. The composition containing perfluoro(2-methylene-4-methyl-1,3-dioxolane) according to claim 5, wherein the at least one fluorine-containing compound is at least one compound selected from the group consisting of Compound 1-6,

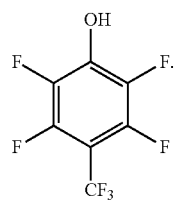
1-6

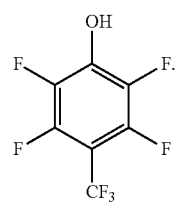
1-6

15. The composition containing perfluoro(2-methylene-4-methyl-1,3-dioxolane) according to claim 4, wherein the at least one fluorine-containing compound is at least one compound selected from the group consisting of Compound 1-4,

18. The composition containing perfluoro(2-methylene-4-methyl-1,3-dioxolane) according to claim 5, wherein the at least one fluorine-containing compound includes at least one compound selected from the group consisting of Compound 1-4 and 1-6,

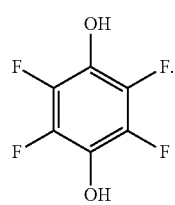
1-4

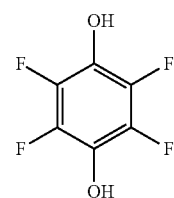
1-4

16. The composition containing perfluoro(2-methylene-4-methyl-1,3-dioxolane) according to claim 4, wherein the at least one fluorine-containing compound includes at least one compound selected from the group consisting of Compound 1-4 and 1-6,

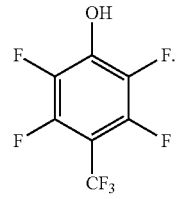
1-6

19. The composition containing perfluoro(2-methylene-4-methyl-1,3-dioxolane) according to claim 5, wherein the at least one fluorine-containing compound is at least one compound selected from the group consisting of Compound 1-4 and 1-6,

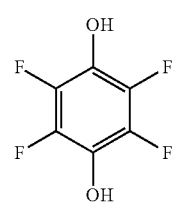
1-4

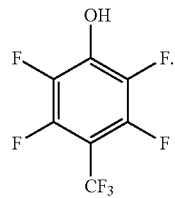
1-6

17. The composition containing perfluoro(2-methylene-4-methyl-1,3-dioxolane) according to claim 4, wherein the at least one fluorine-containing compound is at least one compound selected from the group consisting of Compound 1-4 and 1-6,

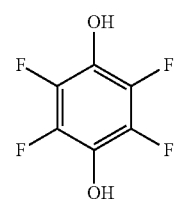
1-4

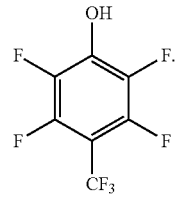
1-6

20. The composition containing perfluoro(2-methylene-4-methyl-1,3-dioxolane) according to claim 5, wherein the at least one fluorine-containing compound is perfluoro hydroquinone.

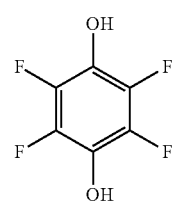
1-4

* * * * *